United States Patent [19]
Joyce et al.

[11] Patent Number: 5,679,535
[45] Date of Patent: Oct. 21, 1997

[54] APPARATUS, KIT AND METHOD FOR THE COLLECTION AND DETERMINATION OF ENVIRONMENTAL ANTIGENS

[75] Inventors: Patrick Joseph Joyce, Blackrock; Edmund Bruce Mitchell, Monkstown; Alan Gaylard Shattock, Scurlock's Leap, all of Ireland

[73] Assignee: University Collge Dublin, Dublin, Ireland

[21] Appl. No.: 302,701

[22] PCT Filed: Mar. 4, 1993

[86] PCT No.: PCT/IE93/00008

§ 371 Date: Dec. 5, 1994

§ 102(e) Date: Dec. 5, 1994

[87] PCT Pub. No.: WO93/18404

PCT Pub. Date: Sep. 16, 1993

[30] Foreign Application Priority Data

Mar. 5, 1992 [IE] Ireland ................. 920700

[51] Int. Cl.[6] .................. G01N 33/543; G01N 33/58
[52] U.S. Cl. ............... 435/7.9; 15/246.2; 15/246.3; 15/347; 73/23.3; 422/56; 422/58; 422/61; 422/83; 422/101; 435/7.92; 435/7.94; 435/7.21; 435/7.31; 435/810; 435/975; 435/287.1; 435/287.2; 436/518; 436/524; 436/807; 436/810
[58] Field of Search ............ 15/246, 246.2, 15/246.3, 347; 73/23.2; 422/55, 56, 58, 61, 83, 101; 435/7.9, 7.92, 7.94, 7.21, 7.31, 810, 975, 287.1, 287.2; 436/518, 524, 528, 531, 533, 534, 164, 169, 805, 807, 810

[56] References Cited

U.S. PATENT DOCUMENTS

| | | | |
|---|---|---|---|
| 2,910,717 | 11/1959 | Raymond | 15/339 |
| 3,972,812 | 8/1976 | Gresl, Jr. | 210/83 |
| 4,632,901 | 12/1986 | Valkins et al. | 422/56 |
| 4,777,021 | 10/1988 | Wertz et al. | 422/101 |
| 4,822,732 | 4/1989 | Sandström et al. | 435/6 |
| 4,833,753 | 5/1989 | Müller | 15/339 |
| 5,153,965 | 10/1992 | Prosser et al. | 15/339 |

FOREIGN PATENT DOCUMENTS 0200381 5/1986 European Pat. Off. .

OTHER PUBLICATIONS

Tovey et al, "The Distribution of Dust Mite Allergen in the Houses of Patients with Asthma", Am. Rev. Respir. Dis., 1981, 124, pp. 630–635.

*Primary Examiner*—Christopher L. Chin
*Attorney, Agent, or Firm*—Felfe & Lynch

[57] ABSTRACT

An apparatus for collecting antigen, including an allergen exemplified by a dust-mite, dispersed in a motile fluid in a given environment that can be inserted in a section of a pipe of a standard vacuum cleaner hose. The apparatus includes a receptacle whose body is formed of nylon, typically with a pore size of from 15 to 60 μm. The receptacle is coated with an antibody that retains the antigen in a contacting relationship. The apparatus is provided with a removable holder, which assists in locating the apparatus in the pipe of the vacuum cleaner. The apparatus can be used directly in an immunoassay for confirming the presence of, or quantifying, the antigen.

26 Claims, 2 Drawing Sheets

APPARATUS, KIT AND METHOD FOR THE COLLECTION AND DETERMINATION OF ENVIRONMENTAL ANTIGENS

TECHNICAL FIELD

This invention relates to apparatus for the collection and detection of antigen and, in particular, to apparatus for collecting, detecting or determining an antigen dispersed in a motile fluid, including air, in a given environment, such as a household environment.

The invention has particular application in the direct detection in the environment of antigens comprising, or derived from, a variety of substances, including micro-organisms, which are causative of disease, especially allergic diseases.

BACKGROUND ART

In recent years it has become apparent that the common allergic diseases viz bronchial asthma, rhinitis and atopic dermatitis are inflammatory disorders. In particular, a number of recent studies have provided convincing evidence that immunological sensitivity to both dust-mite and cat-dander are highly significant independent risk factors associated with the development of asthma. Reports from many different countries have demonstrated a high prevalence of allergy to dust-mites among patients with asthma, ranging from 45–85% (Report of International Workshop of the International Association of Allergology and Clinical Immunology, Bad Krenznach, FRG, September 1987, page 2, Bulletin of World Health Organisation August 1988; and Platts-Mills, T. A. E. and Chapman, M. D. (1987) *J. Allergy Clin. Immunol.*, 80, 6; 755–775).

Mites representing a variety of species, but predominantly those of the species Dermatophagoides, are found wherever local environmental conditions, such as appropriate bedding, carpeting, soft furnishings, humidity and warmth, etc., favour their proliferation. A number of major allergen groups have been defined among the Dermatophagoides species and greater than 80% of mite allergic patients have IgE class antibodies to various allergens associated therewith. However, while the term "house dust-mite" applies to mites of the family Pyroglyphidae, of which ten species have been reported to occur in house dust more often than just occasionally, four species predominate in house dust namely: *D. pteronyssinus, D. farinae, D. microcerus* and *Euroglyphus mayneii*. Other mites found in houses can be important as causative factors of allergic disease and these include mites regarded as storage mites.

Dispersed environmental allergens other than those from dust-mites are also relevant in allergic disease in some patients. Particularly important allergens include those from domestic pets such as cats (cat-dander, Fel dl), dogs and birds, cockroaches and other insects, fungal spores and pollen (Platts-Mills, T. A. E. and Chapman M. D. (1987) (supra)). It is also known that micro-organisms can become dispersed in airborne droplets and transmit disease, a good example being legionnaires' disease, a severe and sometimes fatal, respiratory infection in which ventilation systems are frequently implicated in the transmission thereof, especially in index cases. Furthermore, many diseases may be transmitted by waterborne micro-organisms, for example hepatitis A and cholera.

Many varying factors result in there being wide ranging levels of the aforementioned allergens present at different times and in different households. Allergic disease, from mild to very severe, can result in patients who are sensitive to any of the abovementioned allergens wherever and whenever the particular allergen is present beyond a certain threshold level. No tests yet exist which enable householders themselves to specifically determine levels of any of these allergens in their homes. Thus it is not yet possible for householders to determine, for example, if the cleaning methods they are using to reduce dust-mites or other specific allergens are effective. A commercial semi-quantitative, but non-specific, test known as the "guanine" test (Werner and Mertz, Mainz, Germany) has however been produced, which test correlates with dust-mite numbers only. Guanine is excreted by mites and most other insects and many animals and is therefore not specific to allergy causing mites. The guanine test does not detect the Der pI antigen itself (Platts-Mills, T. A. E. and Chapman M. D. (1987) (supra)) as hereinafter referred to.

The magnitude of environmentally associated allergic disease problems worldwide has led to the holding of International workshops, held under the auspices of the International Association of Allergology and Clinical Immunology and the World Health Organisation, in 1987 and 1990. At these workshops, guidelines concerning the procedures for collecting and processing of dust samples and for laboratory measurement assays, were laid down. These procedures are entirely laboratory oriented and are cumbersome, but nevertheless they have received wide acceptance in clinical laboratories. The following procedures are currently used:

Vacuum cleaners are used to collect dust samples by vacuuming a fixed area for a fixed period of time. The dust is collected into clean paper bags or into an attachment containing a filter made of wire mesh, paper tissue or 4"×10" glass fibre filters. Such collection devices include devices of the type supplied by ALK Laboratories, Inc., Connecticut, U.S.A. Alternatively, techniques such as shaking blankets into a plastics bag or brushing surfaces are also used but are considered less effective. Large particles are then removed by sieving through a 200–300 µm mesh sieve, the objective being to obtain a sample of fine dust that can be accurately weighed. Immunochemical analysis then requires that a fixed weight of dust be extracted into a fixed volume of buffered saline, over a period of 4 hours to release the allergen from the mite faecal particles referred to below.

The predominant allergen in the case of dust-mites has been identified as a cysteine protease of approximately 25,000 M.W., referred to as Der pI, in the case of *D. pteronyssinus* and Der fI in the case of *D. farinae*. These are the so called Group I antigens and they occur not only in the bodies of the mites but more predominantly in the fecal particles excreted by the mites. Other major allergens include those designated as Group II, e.g. Der pII and Der fII, which are also useful diagnostically. Other allergens are designated as Group III and IV. The solubilized dust extract is analysed in an enzyme immunoassay (EIA, ELISA) procedure for the presence of Group I antigens using conventional sandwich immunoassay with mono or polyclonal antibody. The results are expressed as micrograms (or International Units) of allergen per gram of dust by reference to a standard curve constructed with International standard Der pI samples (ex WHO). Such measurement procedures are completely impractical for use by the householder because: a) the dust sample has to be transferred, sieved and weighed from a bag to a smaller container; b) the transferring and sieving of dust from vacuum cleaner bags to collection vessels is dirty an unpleasant and requires the use of a mask and a fume hood; c) sieving dust is laborious and time-consuming and, therefore, expensive in terms of labour; d)

it is impossible to remove all fine dust adherent to the bag; and e) there is a real risk of contamination of a later sample by an earlier sample when dust and fluff trapping dust become lodged in the convolutions of vacuum cleaner hoses and fittings.

Several studies have addressed the issue of volumetric air sampling for house dust-mite allergens (Swanson, M. L. et al. (1985), J. Allergy Clin. Immunol. 76; 74–79, Platts-Mills, T. A. E. et al. (1986), J. Allergy Clin. Immunol. 77; 850–857 and Price, J. A., et al. (1990), Lancet 336; 895–897). In these studies, membranes have been used to capture airborne particles and invariably the dust had to be removed from the filter and the antigen extracted prior to assaying. The amount of airborne allergen required to sensitize a person is presently being debated (Price, J. A., et al. (1990) supra). Furthermore, airborne allergen levels are usually very low in the absence of room disturbance. This is because particles bearing dust-mite allergens fall to the floor rapidly. Because of this problems exist with air samplers worn on the person, and these are also bulky and inconvenient.

A discrepancy exists between results obtained by air sampling and expression of allergen content in a known weight of dust obtained from surface sampling of a carpet in the same room. This has been attributed to differences in retention and thus release of small allergen bearing particles by wool and nylon carpets, respectively (Price, J. A. et al. (1990) supra). This discrepancy might be overcome if the sampling technique measured the quantity of allergen recovered per square metre, a measurement index which might be expected to take account of releasability properties of small particles from different materials. It has been recognized that a better measurement would involve the determination of total allergen present per square meter, presently limited by difficulties in assessment of total quantities of allergen and dust collected per unit area (Fell, P., Mitchell, B., Brostoff, J., (1992) Lancet 340, 788–789).

Many bacteria and viruses contaminate environmental fluids and are, therefore, capable of transmitting infection, for example, by water. Examples of diseases transmitted in this way include legionnaires' disease, salmonella enteric fevers, hepatitis A and hepatitis E, polio, viral gastroenteritis and cholera.

An example of a (non-allergic) disease caused primarily by an air or water-borne micro-organism is Legionella (legionnaires' disease).

It is an object of the present invention to provide apparatus for the collection, and optional detection or determination, of antigen dispersed in a motile fluid, including air, in a given environment, which antigen can be described as an environmental antigen, and which apparatus can be readily used at the site of antigen collection.

It is a further object of the present invention to provide apparatus which can be used to monitor the presence and extent of dispersed antigen at a given locus in the environment, so that the requisite action can be taken to rid the environment of said antigen or, alternatively, to minimize the presence of the antigen at said locus, as required.

DISCLOSURE OF INVENTION

The invention provides apparatus for the collection of antigen dispersed in a motile fluid in a given environment, said apparatus comprising means for retaining the antigen when said antigen comes into contact therewith, by virtue of the fluid carrying the antigen impinging on or passing through the apparatus, said means for retaining the antigen being receivable in, or integral with, a device adapted to be positioned intermediate fluid moving means for drawing the fluid through said device and a sweeping attachment, the antigen retaining means being directly usable in a test system for confirming the presence of, or quantifying, said antigen.

The antigen retaining means may capture the antigen when said antigen comes into contact therewith and comprises a surface capable of binding said antigen, said means further being directly usable in an immunoassay for confirming the presence of, or quantifying, said antigen.

According to one aspect of the invention, the means for capturing and retaining the antigen is a surface coated with antibody to said antigen.

When the means for capturing and retaining the antigen is a surface coated with antibody to said antigen, the coated surface can represent the solid phase for an immunoassay. Thus the latter assay can be carried out at the site where the antigen occurs in the environment.

According to one embodiment of the invention, the means for capturing and retaining the antigen is receivable in, or integral with, a device connectible to a fluid suction means, such that the antigen is extracted from a fluid stream sucked therethrough or impinging thereon.

The means for capturing and retaining the antigen in the second embodiment preferably includes a surface which is fluid porous and adapted for binding said antigen.

Devices according to this embodiment of the invention are generally quantitative dust collection devices, optionally comprising an element of the associated immunoassay, which devices are especially suited for use with domestic or commercial vacuum cleaners, including those capable of sucking up liquids such as vacuum cleaners known in the trade as "3 in 1" vacuum cleaners (wet and dry vacuuming), and with higher fluid-flow rates than those encountered with the passive devices hereinabove defined.

Thus according to this embodiment of the invention, the fluid suction means can be the air suction means of a domestic or other vacuum cleaner or other suitable pump.

Alternatively, the fluid suction means can be the liquid suction means of a "3 in 1" domestic or other vacuum cleaner or other suitable pump.

The fluid porous surface can be accommodated in a tube for insertion intermediate the air suction means of said domestic vacuum cleaner and the sweeping attachment thereof.

The antigen binding surface can bind the antigen directly or indirectly.

Preferably, the fluid porous surface is composed of a porous plastics material. One such suitable porous plastics material is porous, sintered styrene.

The fluid porous surface can also be composed of a porous, protein-binding plastics material.

In one aspect of the invention, the fluid porous surface is composed of an element having a shape corresponding substantially to the shape of said device. Preferably, the shaped element consists at least partially of a gauze of a suitable material, such as nylon.

The porous material preferably has pores having an average diameter in the range 5–300 µm, more especially 15–60 µm.

Indirect binding of antigen can be achieved by means of an antibody bound to said surface. For example, the antibody can be bound to the surface by means of particles coated with said antibody. Thus, for example, antibody may be absorbed directly or indirectly onto latex particles (0.05–20 μm, more especially 0.5 μm in diameter) in conventional manner, which coated particles in turn can be absorbed onto the antigen binding surface.

Alternatively, the binding of antigen can be achieved by entrapment or electrostatic binding.

A device according to the invention can optionally include a fluid porous disc for entrapment of large debris such as fluff and stones in said fluid stream upstream of said surface.

The antigen binding surface can be removable for detection of the antigen.

Alternatively, the detection of antigen can be carried out with the antigen-binding surface in situ following detachment of the device from said fluid suction means.

The device can be adapted to receive antigen detecting means.

A device according to the invention can also include means such as a filter for collecting a major proportion of the dust in a fluid stream passing therethrough or impinging thereon.

The antigen is preferably detected bny enzyme immunoasay in accordance with the invention. A preferred enzyme immunoassay is a sandwich assay.

The antigen binding surface can represent the solid phase of the immunoassay.

The device can also include means for indicating the fluid flow through the device, such as a tensioned vane.

As indicated above the device may contain a tensioned vane or other suitable device to indicate the fluid-flow rate through the device. This may help to confirm, or may be used to indicate, the time required for sampling the material to be tested.

Detection of antigen in accordance with the invention can be quantitative, semi-quantitative or non-quantitative.

The detection of antigen can involve a change in the colour of the antigen binding surface or a part thereof.

Antibody coating of surfaces in accordance with the invention is carried out in conventional manner such as by means of direct absorption or by covalent binding of an optimum concentration of antibody thereto.

The environment in which the apparatus according to the invention can be used may be the household environment.

The antigen may be airborne and/or water-borne.

The antigen is suitably any micro-organism, fungus or allergen.

The apparatus in accordance with the invention is particularly suitable for detecting allergens. Representative of such allergens are dust-mite allergen, cat-dander, dog-dander, insect allergens, such as cockroach allergen, pollen arid fungal spores.

The apparatus in accordance with the invention is also suitable for detecting antigen from a micro-organism which is a member of the Legionella species or a fragment thereof.

The invention also provides means for collecting or for capturing and retaining antigen for use in apparatus as hereinbefore defined, said means comprising immobilized antibody for said antigen.

The invention further provides a kit comprising apparatus as hereinbefore defined as one or more component(s). The kit preferably includes means for the detection of antigen collected by the apparatus.

The invention also provides an extraction medium for use with the apparatus as hereinbefore defined for detecting dust-mite allergen, which medium comprises a buffer containing a dust-mite allergen extracting amount of chitinase.

Apparatus according to the invention are most suited for collecting samples in moderate or high air-flow rates. Such apparatus will generally be devices in the form of attachments, made of any suitable material, preferably plastics, to fit into or between standard vacuum cleaner hose pipes. For example, the apparatus can be placed in the working end of the hose pipe or inserted between the latter and the usual type of accessory attachment for sweeping carpets, normally provided with such appliances.

The device can comprise a tube which is adapted to receive an element which includes a surface capable of binding an airborne or dust-borne antigen. The latter element can also serve as the "solid phase" of the immunoassay used to detect the antigen. The element can comprise a disc of an air porous material such as porous sintered styrene with pore sizes in the range of 5–300 μm of the type manufactured by Porex Technologies, Georgia, U.S.A.

The immunoassay can be used to quantitatively determine the amount of antigen collected by the device. By employing a vacuum cleaner in its usual purpose of cleaning carpets, soft furnishings, etc. with the device in place, dust and other material containing the antigen will be trapped upon and within the air porous material by air being sucked through or passed the porous disc. The user will be directed to vacuum clean an area of a carpet specified, such as approximately 1 $m^2$ for a period of, for example, one minute, in a room being assessed. As indicated above, the porous disc can be made of a material suitable directly or indirectly for binding the antigen being detected. After vacuum cleaning the test site in the specified manner, the user will then remove the wad of fluff, hair, stones, etc. from the porous disc by either knocking it out by tapping, by physical removal or by removing an optional porous pre-filter installed for this purpose. The porous pre-filter suitably comprise a coarse plastics mesh.

The porous assay disc can be removable and the assay carried out in a separate assay unit. However, a preferred technique is to retain the disc in the device and to insert an absorbent plug or the like downstream of the disc (i.e. the end proximal to the vacuum cleaner suction) whereby the plug absorbs the test reagents used to carry out the immunoassay.

Alternatively, the device with the porous disc in situ may be stood upright in a tray or unit capable of collecting fluids, so that test reagents reacting with and passing through the disc are collected therein. When an absorbent plug is used, the test reagents can be collected therein by virtue of gravity, suction or capillary action of said absorbent plug in known manner.

Another type of element for use in the device is a strip of plastics material, optionally coated with a capture antibody for the detection test. Such strips can be inter alia flat, curved or spiral. The strips may be provided with holes. Furthermore, the strips can be provided with projections or convolutions to increase the surface area thereof. In practice, almost any shape will suffice for the element provided that it has a sufficient surface area to collect enough dust in a given time period, but the element should obviously not be of a size which would block the pipe wherein it is accommodated and impede the airflow to such an extent that the vacuum cleaner no longer sucks up sufficient dust. The strip may be a device known as a dipstick, for example, a dipstick of the type manufactured by Micronic BV, Lelystad, the Netherlands (Cat. No: 813-05). Such a dipstick may be simply held by any convenient means in the attachment in the airstream in the pipe in such a way that the air stream impinges on and is deflected thereby. It is even possible to hold the dipstick or other strip used manually in the airflow controlling vent, usually fitted as standard to most modern domestic vacuum cleaners.

If the strip is coated with a non-drying "sticky" agent such as glycerol, agar or gelatin, the impinging dust will adhere better thereto and binding will be assisted by static charges. In the event that the strip or dipstick is not coated with an antibody, then the requisite antibody will generally be coated on the walls of the assay vessel wherein the detection assay is carried out.

An especially preferred device is one which permits the user to quantify the amount of antigen present per unit area. This type of device is particularly suitable for detection of an allergen such as house dust-mite or cat-dander. Quantification of allergen per unit area is especially important in order to assess clinically significant amounts of allergen (Price, J. A., et al. (1990) supra).

The element for collecting the dust for use in the device may consist of any suitable tubular, conical or other suitably shaped element. Preferably, the shaped element comprises a gauze sieve made of any suitable material, most especially plastics material, and which permits all or a portion of the airflow to pass therethrough, whereby a major proportion, more especially greater than 75%, of dust in the portion of air passing therethrough is trapped and retained by said gauze element.

Suitable gauzes for use in the shaped element are marketed by GVS Srl, Bologna, Italy, in the form of tubular filters. An especially suitable such tubular gauze filter is one with a 40 µm nylon mesh, more especially type FI/64-4. However mesh sizes are not crucially important because dust-mite particles (generally 10–40 µm) often adhere to larger dust particles, etc. and will be retained by the filter, even if the apertures in the gauze are quite large. Thus as indicated above, gauzes with mesh sizes from 5–300 µm can be used.

The gauze is preferably coated with monoclonal or polyclonal antibody. However, alternatively, the gauze need not be coated with antibody and in this situation the apparatus would optionally include a detachable dipstick, the latter dipstick being disposed in, or attached to, but detachable from the gauze filter device. Such an arrangement avoids the necessity of having to remove the dust/extraction buffer mixture from the gauze before continuing with the immunoassay. If a dipstick is included, it is preferably coated with the first antibody of the immunoassay. It will be appreciated that it is not essential for the dipstick to be included as part of the dust collection device during collection, since it may be incorporated in the test system after dust collection as hereinafter described.

Indeed, the gauze device as such can serve as a collecting device which is superior to any other currently available collecting system, as hereinafter described.

In the case of the detection of airborne allergens, instead of sampling carpet or soft-furnishings, it may be more appropriate to sample the air in a room for airborne allergenic fomites such as the dust-mite fecal particle, pollen, etc.

The detection assay for house dust-mite will normally involve an antigen extraction procedure as a first step.

Dust mite allergens are found in both the body of the mite and its faecal particles. The fecal particles persist for long periods and their accumulation in fabrics and furnishings results in about 95% of the Group I antigen being mite fecal particle-associated. At present Group I antigen is used as the index of clinical exposure. The fecal particles consist of food balls coated in a peritrophic membrane (Platts-Mills, T. A. E. and Chapman M. D. (1987) supra) which contains chitin. The allergen is not, as hereinafter demonstrated in Example 3, reliably solubilized in a short time in simple buffers. Thus it has been found that the dust should be suitably extracted with PBS containing a surfactant such as TWEEN 20 (TWEEN is a Trade Mark) at a concentration of 0.5% (PBST) for 30 min. to 4 hours before carrying out the immunoassay. Furthermore, it has been found that with PBST that it is possible to repeatedly extract the same sample of dust and to obtain more allergen with each extraction. Thus it would appear that the known extraction method described above does not efficiently extract the dust-mite allergen.

An especially suitably extraction medium for use in an immunoassay for the detection of dust-mite allergen in accordance with the invention is an extraction buffer consisting of PBS pH 6.0 containing 0.03% chitinase and 0.5% TWEEN 20, but these concentrations are not critical. With this extraction buffer the optical densities (ODs) obtained are raised by between 20–50%.

An especially efficient means for extracting dust-mite antigen has been found to be ultrasonication. The latter technique has been found to be more efficient than any detergent systems used, including TWEEN 20 per se. However, ultrasonication is obviously not suitable for a test to be carried out by the layman.

As indicated above, the preferred immunoassay detection technique is enzyme immunoassay. However, it is possible to use many known immunoassay techniques.

For example, it would be possible to use a radio immunoassay. However, this would obviously not be advisable for safety reasons since the assay is primarily intended for use by unskilled laypersons.

The most suitable assay is that known as a "sandwich" or "capture" assay wherein the antibody component of a reactable antigen antibody combination is insolubilized onto the solid phase and allowed to react with or "capture" the antigen forming an antigen/antibody complex, which can be detected by means of a second antibody conjugated to a suitable enzyme such as horseradish peroxidase (HRPO) or alkaline phosphatase (AP), reacting with the complex or by enzyme amplification reagents such as streptavidin/biotin using methods well known to those skilled in the art. After washing, the bound conjugate is detected with a suitable tracer. In this enzyme immunoassay procedure, such a tracer would be a substrate/chromogen for the enzyme, producing a color approximately proportional in intensity to the amount of antigen present in, or on, the assay device. Conventional chromogens include o-phenylenediamine (OPD) or 3,3', 5,5'-tetramethylbenzidine dihydrochloride (TMB) or 2,2'-azino-bis(3-ethylbenzthiazoline-6-sulphonic acid) (ABTS) which is easier to read by eye where the enzyme is HRPO and p-nitrophenylphosphate (PNPP) where the enzyme is AP. If it is desired that the test result be retained (stored) for long periods on the discs, membranes or dipsticks, as appropriate, the product of the enzymatic reaction should be insoluble. Such substrates with insoluble products include di-aminobenzidine (DAB) or 4-chloronaphthol for HRPO and 5 bromo-4-chloro-3-indolyl phosphate (BCIP) for alkaline phosphatase.

In a two-antibody sandwich assay the antibodies may be either monoclonal or polyclonal. The preferred method is to use a single monoclonal antibody or mixture of monoclonal antibodies on one side of the "sandwich" to obtain specificity and a polyclonal antibody on the other side in known manner. Either may be used as the conjugated antibody.

An alternative method to the more commonly used immunoassay methods where the antigen is "captured" by a solid-phase bound antibody, is to use a material which directly binds the antigen by natural means such as electrostatic binding. Examples of such materials are polyethylene porous membranes marketed by Porex Technologies (supra) (e.g. Cat. Nos. X-4916, X-4897 and X-4899). The bound allergen is then detected by a specific, preferably monoclonal, antibody which may be conjugated for detection purposes or the reaction thereof may be detected by any convenient anti-species antibody in the "indirect" technique well known to those skilled in the art.

Antibody coated dipsticks which can be used in the devices according to the invention can also be analysed by conventional immunoassay techniques such as ELISA, by dipping them sequentially into an extraction/wash solution, conjugated second antibody, wash solution and substrate in conventional manner. The test result is determined by comparing the colour produced in the substrate solution with positive controls or with a colour chart.

If the dipstick is not coated with antibody or only coated with a sticky layer then, after sample collection as described, the dipstick is inserted into an immunoassay well coated with the first antibody. Extraction buffer is then added to solubilize the antigens or allergens adhering to the dipstick. Released antigen/allergen will then bind to the first antibody bound on the well and the wells can then be washed, conjugate added, washed again and substrate/chromogen added in conventional manner.

In the case of a typical device after vacuum cleaning a prescribed area the user removes the gauze filter from the cleaner hose or tube. The filter is then inserted into a suitable container and an extraction/wash solution is added. An antibody coated dipstick, if employed, is then detached or placed (if provided separately) into the gauze filter and is used to gently stir the dust/extraction buffer mixture, which is then left to incubate for a short period so that the solid phase antibody can bind the allergen extracted from the dust. The dipstick is then removed, rinsed in tap-water or buffer to remove visible dirt and then dipped sequentially in the wash, conjugate, wash and substrate solutions in conventional manner. The result is 'read' by comparing the colour developed on the dipstick with colour bars on a standard chart.

In an especially preferred device the tubular gauze filter is coated with antibody to the required allergen as described. After vacuum cleaning the suggested area(s) the user removes the gauze filter containing the dust sample from the holder and places it in the allergen extraction buffer contained in the first tube of a set of tubes (cassette). The allergen in the dust sample is extracted and binds to the antibody on the gauze filter itself. After a short period the filter is removed and the dust washed out under running water from a tap; the device is then placed in the second tube of the cassette, containing anti-allergen enzyme conjugate, which will bind to the allergen. After a further short period, the device is further rinsed under running tap water and then placed in the third tube of the cassette, containing a substrate and chromogen suitable for the enzyme. The color developed in the substrate after a stated time period is compared with a printed colour scale affixed around the base of this tube. The colors correspond with specific amounts of allergen per $m^2$.

Figure 1:
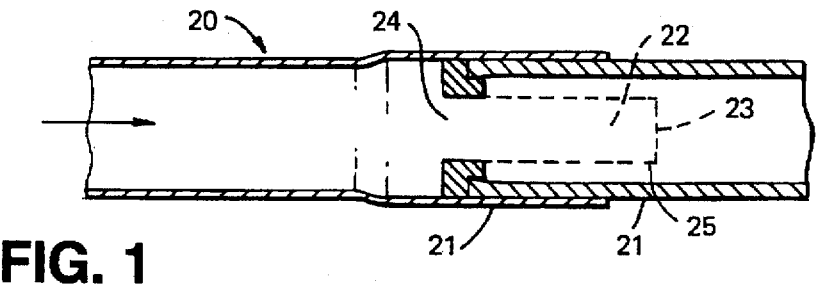
FIG. 1 is a schematic representation of apparatus according to a first embodiment of the invention in situ in a pipe of a conventional domestic vacuum cleaner.

In the accompanying figures arrows unaccompanied by reference numerals indicate direction of air flow.

BEST MODE FOR CARRYING OUT THE INVENTION

Figure 2:
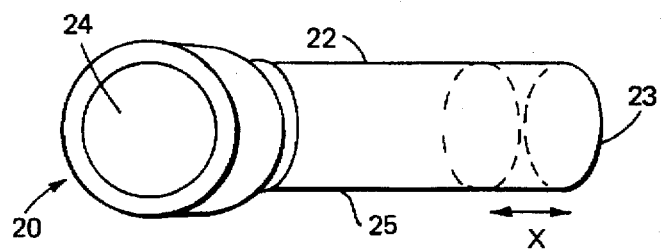
FIG. 2 is a further schematic representation of the apparatus of FIG. 1.

Referring to FIGS. 1 and 2 of the Drawings, there is indicated generally at 20, apparatus of the type hereinbefore referred to and which is adapted to be inserted into one section of a pipe 21 of a standard vacuum cleaner hose. The apparatus 20 consists of a generally tubular receptacle 22 having a base 23 and a mouth portion 24 connected by a pair of opposed ribs (not shown), the mouth portion 24 being of a wider diameter than the remainder of the receptacle 22 and facilitating insertion of the apparatus 20 into the pipe 21 by means of a snug fit. The body 25 of the receptacle 22, with the exception of the fibs, is composed of a nylon mesh material typically with a pore size in the range 15–60 µm, more especially 40 µm. The remaining parts of the receptacle 22 are composed of a rigid plastics material. In use, dust sucked up in the pipe 21 is collected in the receptacle 22 for subsequent analysis. A pre-filter (not shown) in the form of a removable lid may be provided on the apparatus 20 with a coarse mesh for entrapment of hair and relatively large particles. Thus the dust collected in the apparatus 20 is a relatively fine dust. Following collection of the sample the apparatus 20 is removed for use in an immunoassay for the detection of antigen.

Figure 3:
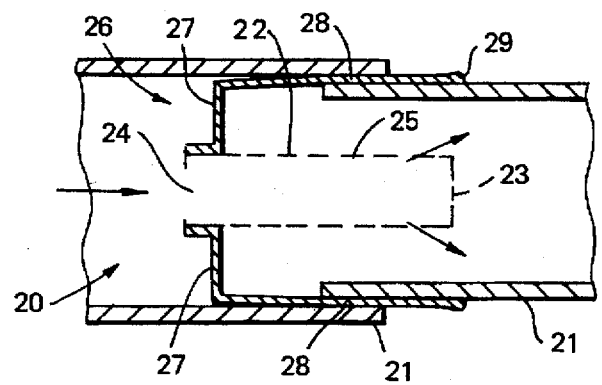
FIG. 3 is a schematic representation of apparatus according to a second embodiment of the invention in situ in a pipe of a conventional domestic vacuum cleaner.
Figure 4:
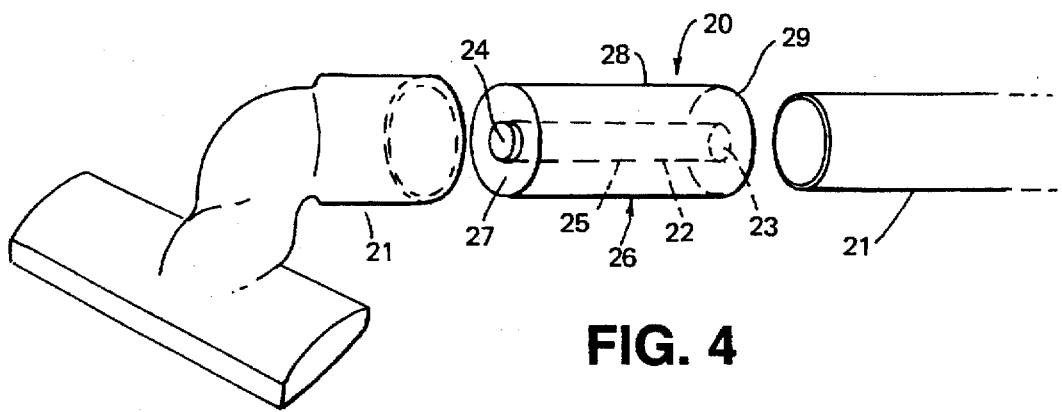
FIG. 4 is a further schematic representation of the apparatus of FIG. 3.

Referring to FIGS. 3 and 4 there is indicated a modification of the device depicted in FIGS. 1 and 2 and wherein like parts are given like reference numerals. Apparatus 20 is provided with a removable holder indicated generally at 26 which assists in locating the apparatus in the pipe 21 of the vacuum cleaner. The holder 26 defines the mouth portion 24 of the apparatus 20 and a pair of shoulders 27 from which depend a skirt 28 receiveable between the overlapping parts of the pipe 21, said skirt 28 being provided at its free end with gripping means 29 which assist in the insertion or removal of the apparatus 20 in use.

Figure 5:
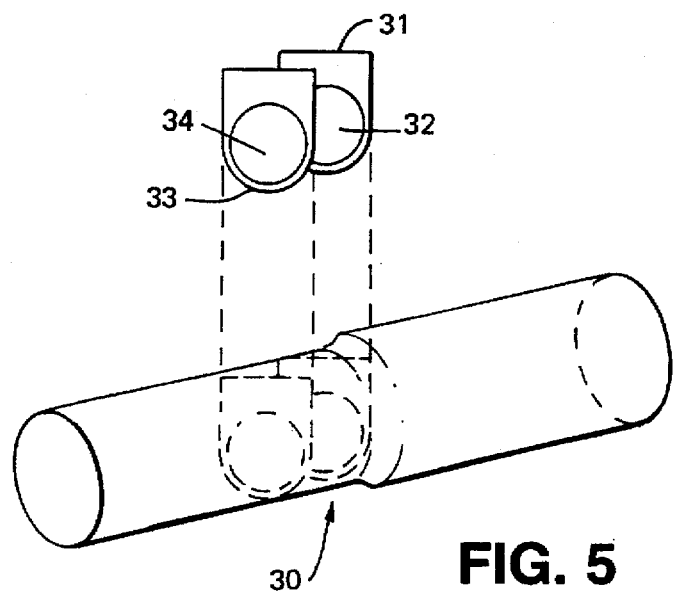
FIG. 5 is a schematic representation of apparatus according to a third embodiment of the invention.

Referring to FIG. 5, there is indicated generally at 30, a further apparatus of the type referred to herein.

The apparatus 30 consists of a holder 31 with a removable air-porous disc 32 for entrapment of airborne allergen, said porous disc 32 having pores with a diameter in the range 5–300 µm, optimally 15–60 µm. The apparatus also includes a pre-filter 33 disposed, in use, upstream of the apparatus 30 and which has a similar construction thereto, except that the pre-filter 33 has a disc 34 with larger pores than the disc 32 and serving the same function as the pre-filter described in relation to FIG. 1. Following collection of the sample, the apparatus 30 is removed for use in an immunoassay.

Figure 6:
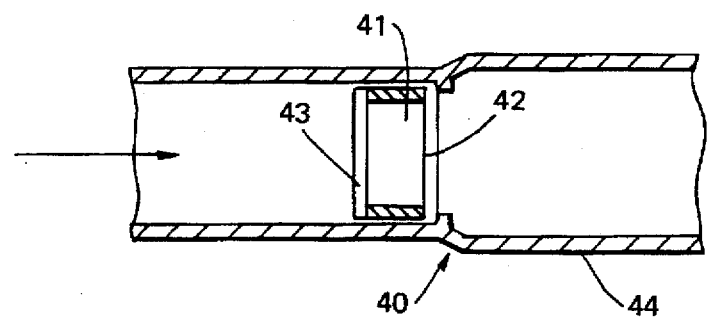
FIG. 6 is a schematic representation of a section of an apparatus according to a fourth embodiment of the invention.
Figure 7:
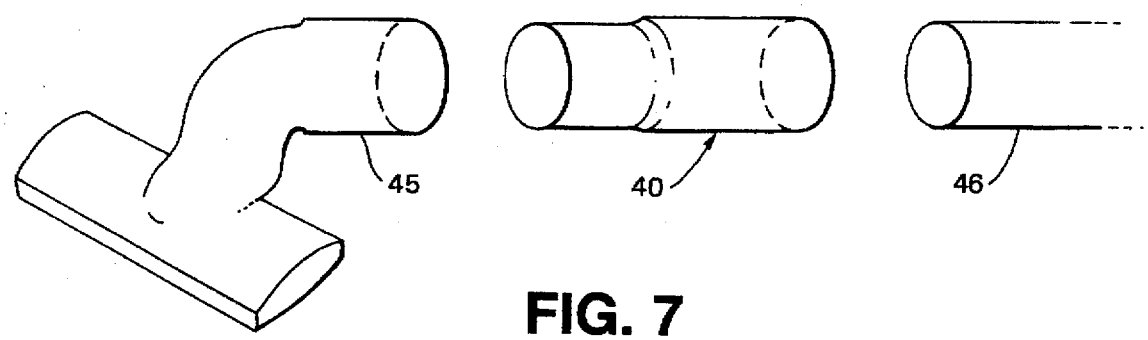
FIG. 7 is a schematic representation of the apparatus depicted in FIG. 6 in relation to the parts of the sweeping attachment of a domestic vacuum cleaner in exploded view.

Referring to FIGS. 6 and 7 of the Drawings, there is indicated generally at 40, a still further apparatus of the type referred to herein.

The apparatus 40 comprises a dust collection receptacle 41 with an integral air-porous disc 42 for the capture of antigens and a porous disc 43 for the collection of hair and relatively large particles of dust, said disc 43 being disposed upstream of the disc 42, in use and removable after use. The apparatus 40 is also provided with an element 44 which is an extension of the receptacle 41, for insertion as a snug fit in the pipe of a domestic vacuum cleaner intermediate the sweeping attachment 45 and a section of the hose pipe 46. Following collection of the sample, the apparatus 40 is removed for use in an immunoassay.

Examples of airborne antigen detection kits in accordance with the invention suitably include the following, in addition to instructions for carrying out the test:

A. FOR VACUUM CLEANER KIT (disc type):

1. A disc holder for insertion into a vacuum cleaner pipe, which can be disposable or reusable;
2. A pre-filter which is optional and can also be reused several times, but is more likely to be disposable;
3. One or more porous assay discs as hereinbefore described, optionally coated partially or completely with antibody to the antigen being detected. Such prepared discs are preferably sealed for individual use and can be supplied in separate packs as refills for the kit device. Alternatively, the holder and assay disc can be supplied together as a bonded, disposable unit;
4. Optionally an absorbent plug for taking up test reagents after passing through the assay disc; and
5. The conjugate and substrate and other components such as wash fluid and instructions required for the test.

B. VACUUM CLEANER KIT (plain dipstick type):

1. Coated dipstick device and simple holder; and
2. Reagents for carrying out the immunological detection of collected antigen typically extraction buffer, conjugate and substrate.

C. VACUUM CLEANER KIT (gauze filter+dipstick type):

1. Gauze filter as used in the apparatus depicted in FIGS. 1 and 2 or FIGS. 3 and 4 and as described in Example 6 to fit standard vacuum cleaner hoses;
2. Antibody coated dipstick installed in 1; and
3. Reagents for carrying out the immunological detection of collected antigen, typically including extraction buffer in a vessel designed to accommodate the gauze filter, plus conjugate, substrate, etc.

D. VACUUM CLEANER KIT (gauze filter coated with antibody):

1. Gauze filter as used in the apparatus depicted in FIGS. 1 and 2 or FIGS. 3 and 4 and as described in Example 5.
2. Reagents for carrying out the immunological detection of collected antigen, typically including extraction buffer in a vessel designed to accommodate the gauze filter, plus conjugate, substrate, etc.

The invention will be further illustrated by the following Examples.

In the following Examples references to the standard assay refer to a standard assay for Der pI antigen in accordance with the method of Luczynsk, C. N. et al. (1989) J. Immunological Methods, 118, 227–235 (reagents were a gift from Dr. M. Chapman, University of Virginia, Charlottesville, Va., U.S.A.).

Dust mite allergen levels and their significance are expressed as follows in accordance with current accepted criteria:

<2.5 µg/g dust=low, not likely to cause sensitization
2.5–5 µg/g=low, might cause sensitization
5–10 µg/g=moderate, may cause sensitization
>10 µg/g=high, likely to cause sensitization, and exacerbation in sensitized persons
>25 µg/g=very high Furthermore, in the following Examples the following materials and methods are common.

Positive control material used was "spent medium" i.e. the powder residue left after cultivating house dust-mites on ox liver powder. Where this was used as positive control, normal ox liver powder was used as negative control.

Negative controls consisted of normal ox liver powder or, in most experiments, dust containing <2.5 µg/g Der pI antigen.

In all experiments, buffer consisting of 0.5M sodium carbonate buffer pH 9.6—carbonate coating buffer (CCB) was used for coating antibodies onto the solid-phases. "Quenching" of unbound sites was carried out with 1% bovine serum albumin (BSA) in CCB.

Two extraction buffers were used, a first buffer referred to herein as EB1, containing phosphate buffered saline, pH 6.8 and 0.5% TWEEN 20, and a second buffer referred to herein as EB2, containing 0.03% chitinase (Sigma, Cat. No. C1525) in phosphate buffered saline pH 6.0.

Washing was carried out with TrisHCl buffer at pH 7.2 or tap-water as indicated.

For laboratory plate assays the substrate/chromogen solution used was 3,3,5,5-tetramethylbenzidine dihydrochloride, (Sigma T8768), 0.125 mg/ml final concentration in 0.2M citrate-phosphate buffer pH 5.0 containing 3 µl of 30% analytical grade hydrogen peroxide in 10 ml substrate.

A monoclonal anti-Der pI antibody (MAB) was used for coating in all experiments at a dilution of 1/1000 in CCB. Antibody was isolated by standard techniques, using Der pI antigen prepared from spent medium by extraction with PBS containing 0.5% TWEEN 20 as the innoculum for Balb/c mice. Clones were screened with spent medium PBS extract. Reactive IgG clones were checked for non-reactivity with normal ox liver powder. MAB was produced as ascites and tissue culture fluid.

Conjugates were made using rabbit antiserum to Der pI antigen, prepared by innoculating rabbits using standard protocols with Der pI antigen extracted from spent medium as above. Extracted antigen was shown to have a high degree of homogeneity by polyacrylamide gel electrophoresis (PAGE). The IgG fraction of the antiserum was prepared by ion-exchange chromatography (Whatman DE52) and conjugated to horse-radish peroxidase (Sigma, Cat. No. P8375) as previously described (Shattock, A. G. and Morgan B. M., J. Med. Virol. 1984, 13, 73–82). Conjugates were diluted 1/200 in PBS containing 1% BSA and 50 mg/ml of cytochrome C (Sigma, Cat. No. C7752).

EXAMPLE 1

Modified assay for house dust-mite allergen

A modified version of the standard assay (Luczynsk, C. N., et al. (1989) supra), hereinafter referred to as the U.C.D. modified assay, was developed and was carried out generally as follows:

1. 8-well polystyrene microtiter flat well strips (Nunc, MAXISORB grade (MAXISORB is a Trade Mark)) were coated with 100 μl of monoclonal antibody (MAB), diluted 1/1000 in CCB, for 18 hours at 4° C. and quenched for 1 hour;

2. 100 μl of the sample extracts to be tested were placed in each well. 100 μl appropriate positive and negative controls (see below) were included in every run. Test wells were incubated for 1 hour at 20° C. and then washed four times in an automatic Organon ELISA plate washer, with one minute "soak" intervals between washes;

3. 100 μl of conjugate (see below) were added to each well and incubated for 1 hour at room temperature (circa 20° C.) and then washed five times, as above;

4. 100 μl of substrate/chromogen were added and incubated for 10 min. at room temperature; and 5. The absorbance of the wells was read at 450 nm in an SLT spectrophotometer.

The results obtained when samples of extracted antigen from various loci in a house were assayed by the standard assay and the UCD modified assay are indicated in Table 1.

TABLE 1

| Site (1 m²) | Standard Assay Der pI μg/g | Modified Assay Der pI μg/g | O.D. |
| --- | --- | --- | --- |
| Dining-room | 13.40 | 22.00 | 0.894 |
| Bedroom | 3.40 | 8.00 | 0.499 |
| Bedroom | 30.00 | 46.00 | 1.475 |
| Bedroom | 27.20 | 30.00 | 1.085 |
| Dining-room | 33.20 | 36.00 | 1.233 |
| Kitchen | 9.00 | 4.00 | 0.402 |

These results show that there is a good agreement between the standard and U.C.D. modified assays. However, the U.C.D. modified assay is simpler to carry out and is more sensitive (see Example 2) and was, therefore, retained for all further evaluations.

EXAMPLE 2

Assay Sensitivity

Dilutions of dust-mite "spent medium" (i.e. the residue of medium used for cultivating live dust-mites on ox-liver powder) which can be described as artificial dust were made to give the protein concentrations listed in Table 2. Only a small proportion of the "spent medium" is Der pI protein. These dilutions were tested in both the standard assay and the U.C.D. modified assay, giving the results shown in Table 2. It can be seen that the U.C.D. modified assay is more sensitive than the standard assay. When the purified Der pI WHO standard was tested in the two assays, the U.C.D. assay was able to detect <3 ng of allergen, whereas the standard assay could only detect down to 12 ng allergen.

TABLE 2

Assay readings for "spent medium"
Standard assay vs U.C.D. modified assay

| Protein conc. (total) | Standard assay O.D. | U.C.D. modified assay O.D. |
| --- | --- | --- |
| 1 mg/ml | 1.936 | 2.315 |
| 0.5 mg/ml | 1.937 | 2.258 |
| 50 μg/ml | 1.795 | 2.253 |
| 5 μg/ml | 1.121 | 1.574 |
| 0.5 μg/ml | 0.236 | 0.490 |
| 50 ng/ml | 0.199 | 0.198 |
| Negative control | 0.191 | 0.096 |
| Negative control | 0.178 | 0.078 |

O.D.s are means of duplicate wells in all cases.
Positive cut-off = 2x negative control.
Samples above the dotted line are positive.

It can be seen that the U.C.D. modified assay is substantially more sensitive for detecting allergen in "spent medium" than the standard assay.

EXAMPLE 3

Chitinase PBST v PBST in extraction of dust-mite allergen

An experiment was carried out to compare the conventional PBST extraction buffer with a buffer containing chitinase. The assay method used was the U.C.D. modified assay of Example 1. The extraction time used was one hour for each of the standard PBST extraction EB1 and the chitinase extraction EB2. The results are shown in Table 3.

TABLE 3

| Sample | O.D. EB1 | O.D. EB2 |
| --- | --- | --- |
| Low level (<50 μg/g) | 0.224 | 0.393 |
| Low level (different) | 0.215 | 0.473 |
| Medium (100–170 μg/g) | 0.726 | 0.942 |
| Medium (different) | 0.544 | 0.632 |

Samples with high levels of antigen were not included as they go off-scale in both systems.

It will be observed that there is a significant improvement in O.D. with chitinase extraction buffer EB2 relative to the extraction buffer EB1 which contains PBST only.

EXAMPLE 4

Method for detecting house dust-mite allergen with a dipstick held in a domestic vacuum cleaner pipe.

1. Polystyrene dipsticks were coated with 750 μl of 1/1000 monoclonal anti-Der pI antibody (MAB) for 18–20 hours at 4° C. The dipsticks were then coated in neat glycerol.

2. For the test, a dipstick was inserted into the air-control vent at the upper end of a VAX (VAX is a Trade Mark) vacuum cleaner pipe and held in place by SELLOTAPE (SELLOTAPE is a Trade Mark) for the purposes of the experiment. The area to be tested was then vacuumed as above.

3. A dust sample and negative and positive control samples with known amounts of antigen, determined by the standard method, were placed in trays or on pieces of clean carpet and vacuumed for approximately one minute per sample, a new dipstick being used for each sample.

4. The dipsticks were then placed in a tube with 750 μl of extraction buffer EB1 and mixed occasionally during an incubation period of 1 hour. The dipstick was then washed for 1 minute from a wash bottle and placed into 750 μl conjugate for 1 hour at approximately 20° C. The dipsticks were again washed for 1 minute and then placed in 750 μl of substrate/chromogen for 10 minutes followed by 750 μl of 4N sulphuric acid to stop the reaction. 200 μl of substrate was then removed to a microtitre well for reading in an SLT spectrophotometer at 450 nm.

O.D. readings for controls and a test dust sample are given in Table 4.

TABLE 4

| Sample | O.D. |
| --- | --- |
| Negative control (liver powder) | 0.134 |
| Positive control (spent medium) | 0.353 |
| Test dust sample (>100 μg/g)* | 0.643 |

*According to standard assay.

EXAMPLE 5

Method for detecting house dust-mite allergen using an antibody coated tubular type air-porous gauze filter device mounted in the piping of a domestic vacuum cleaner 1. Tubular filters with 40 μm nylon mesh (GVS Srl Type FI/64-4) were placed open end up in a beaker of sufficient size, and 1/1000 coating MAB was added to give a depth sufficient to coat region X in FIG. 3. Coating was carried out for 18–20 hours at 4° C., followed by quenching for 1 hour at 37° C. with 2 ml 1% BSA in PBS containing 5% analytical grade sucrose (BDH) to block unbound sites and to stabilise the antibody to drying, which was carried out for 3 hours at 37° C. in a non-humidified incubator.

2. Because the filters were not designed for the purpose to which they were put in accordance with the invention, the mounting of the filters in the vacuum cleaner pipe was by means of a discarded plastics container commonly used for containing 35 mm film cassettes; a hole was cut in the base of this plastics container with a drill and file. This "holder" was used in a manner so as to ensure that all of the air being sucked through the cleaner passed through the filter, similar to the holder of the apparatus depicted in FIGS. 3 and 4.

3. Selected sites containing high, medium, low or no allergen levels were then vacuum cleaned, each over one ¼ metre square area, for a period of approximately 30 seconds per area.

4. Each device was removed and placed into a 15 ml "universal" plastics specimen tube containing 5 ml extraction buffer, EB1. The devices were then stirred for about 30 seconds and then left to stand for 10 minutes, the extracted allergen being then bound by the solid-phase antibody on the nylon gauze.

5. The devices were then removed and washed under cold running tap-water, open end down, until all the visible dust was washed away (about 1 minute).

6. The devices were then placed in a tube with 1 ml conjugate and incubated for 10 minutes at room temperature (degree 20° C.).

7. The devices were then washed under running tap-water for 1 minute and placed in 1 ml substrate for 10 minutes, after which a 200 μl sample was mixed with 200 μl of 4N sulphuric acid and read in an SLT spectrophotometer at 450 nm.

For home use, neither acid nor spectrophometric reading would be required and the results would be read by comparing the colour obtained in the robe of substrate with a colour scale printed on a strip and affixed around the lower circumference of the tube.

The results are given in Table 5.

TABLE 5

| Sample | Mean O.D. |
| --- | --- |
| Negative | 0.0375 |
| Negative | 0.0245 |
| Low level | 0.702 |
| Low level | 0.600 |
| Medium | 1.010 |
| Medium | 0.921 |
| High level | 1.088 |
| High level | 1.085 |

The high sensitivity should be noted.

EXAMPLE 6

Method of detecting the house dust-mite allergen employing a non-coated tubular gauze filter and an antibody coated dipstick for detection 1. Dipsticks were coated with MAB as in Example 4 above.

2. Dust was collected in the filter as described in Example 5, steps 2 and 3, but the filter was used uncoated.

3. The filter was then placed in a "universal" specimen container and 5 ml of EB1 was added.

4. A coated dipstick was then inserted into the filter and gently rotated in order to mix the dust with the EB1 and remove trapped air. The dipstick was then left in the mixture to "capture" extracted antigen for 15 minutes.

5. The dipstick was then rinsed with running tap-water for 1 minute.

6. The dipstick was then placed in 750 μl of conjugate and incubated for 1 hour at room temperature.

7. The dipstick was then washed under running tap-water and placed into 750 μl of TMB substrate for 10 minutes. 200 μl of the substrate was then transferred to a standard microtitre well with 200 μl of 4N sulphuric acid and its absorbance was measured at 450 nm in an SLT microtitre spectrophotometer. For domestic use the sulphuric acid would not be required and the result would be read by comparing the colour of the substrate with a supplied chart.

The results are shown in Table 6.

TABLE 6

| Room | Site in room (1 m²) | Dipstick in uncoated tubular filter | |
|---|---|---|---|
| | | Der pI µg/g | O.D. |
| 1st House | Beside fireplace | 0.4 | 0.113 |
| Dining-room | centre | 11.2 | 0.766 |
| Bedroom 1 | Left of bed | 4.8 | 0.418 |
| | Right of bed | 0.8 | 0.144 |
| Bedroom 2 | Between beds | 12.0 | 0.879 |
| | Beside wardrobe | 14.8 | 1.020 |
| Bedroom 3 | Beside bed | 11.2 | 0.789 |
| | Beside window | 6.0 | 0.508 |
| 2nd House | Fireplace | 14.0 | 1.010 |
| Dining-room | centre | 8.0 | 0.640 |
| Kitchen | Near kitchen | 0.4 | 0.116 |
| | Near door | 4.0 | 0.376 |

EXAMPLE 7

Method for passively detecting house dust-mite allergen.

1. Polystyrene wells (12-well Tissue Culture Clusters, Costar, Cambridge, Mass. U.S.A.) were coated with 500 µl of MAB for 18–20 hrs at 4° C., quenched for 1 hour and coated with glycerol. For a given test, three wells were coated with extracts of Der pI antigen at a high, medium and low level, respectively, and sealed with tape. A single test well was left open on the floor and a small quantity of allergen containing dust was sprinkled in the air about two metres above the plate. A further test plate was left exposed on a bench for 72 hours in a laboratory where positive samples were being handled, the control wells being sealed.

2. The sealing tape on the wells was removed and the EIA detection test was carried out as described in Example 1, except that the reagent volumes added were increased throughout to 500 l and washing was by means of a jet of buffer from a plastics wash bottle.

EXAMPLE 8

Use of tubular gauze filter to detect microorganisms in water

Tubular gauze filters (GVS FI/64-4) were coated at the bottom 1 cm with high-titer human antibody to hepatitis A virus (HAV) (obtained from volunteer donors) at a dilution of 1/100 in CCB, overnight at 4° C. By arranging a funnel with built-in tap in a stand with the tubular filter also clamped in the stand so that the outlet from the funnel was inside the top (open) end of the tubular device, it was possible to allow fluid from the funnel to drip through the device responsible slowly (approximately 1 litre in 1 hour). A litre of water into which was put 100 µl of inactivated hepatitis A antigen (A gift from Cambridge Biotech Ltd, Gateway, Ireland) was passed through the device. The device was then placed in a tube containing a different human anti-HAV conjugated to HRPO (as above) and incubated at room temperature for one hour. The device was then rinsed for 30 seconds in several changes of PBST and then placed in TMB substrate in a tube. After 15 minutes 50 µl was removed to a microwell strip and 50 µl of 4N $H_2SO_4$ added. The colour was read at 450 nm.

EXAMPLE 9

Reliability of retention of dust by the apparatus according to the invention

Tubular gauze devices were weighed. 0.5 g of 300 micron mesh sieved dust samples, obtained in three houses, were sprinkled over a clean area of approximately $\frac{1}{10}$ m² of vinyl flooring material and vacuum cleaned in a manner similar to that used for cleaning carpets, over a 30 second period. The device plus retained dust was then weighed. This was repeated for a total of ten samples in each of two experiments carried out on two days. The amount of allergen present in the original (sieved) dust and retained dust was also measured, using the UCD assay. The purpose was to determine what proportion of dust was reliably retained by the device according to the invention in the normal sampling time of 30 seconds.

The results are indicated in Table 8.

TABLE 8

Retention of dust and allergen by apparatus according to the invention

| Sample | Weight dust retained | % retained | Der pI retained (µg/g) | Der pI original sample (µg/g) |
|---|---|---|---|---|
| | | FIRST EXPERIMENT: | | |
| 1 | 0.412 | 82% | 4.0 | 6.4 |
| 2 | 0.471 | 94% | 28.8 | 28.8 |
| 3 | 0.467 | 93% | 3.2 | 1.6 |
| 4 | 0.466 | 93% | 2.4 | 4.0 |
| 5 | 0.455 | 91% | 36.0 | 27.2 |
| 6 | 0.463 | 92% | 14.0 | 14.4 |
| 7 | 0.430 | 86% | 8.0 | 23.2 |
| 8 | 0.430 | 86% | 10.0 | 4.8 |
| 9 | 0.475 | 95% | 23.2 | 24.0 |
| 10 | 0.456 | 91% | 5.6 | 6.4 |
| | | MEANS: | 13.52 | 14.02 |
| | | SECOND EXPERIMENT: | | |
| 1 | 0.496 | 99.2% | 16.0 | 17.6 |
| 2 | 0.489 | 97.8% | 18.0 | 16.0 |
| 3 | 0.461 | 92.2% | 10.0 | 12.8 |
| 4 | 0.410 | 82.0% | 1.6 | 1.6 |
| 5 | 0.409 | 81.8% | 1.6 | 1.6 |
| 6 | 0.448 | 89.6% | 25.0 | 22.4 |
| 7 | 0.460 | 92.0% | 4.0 | 4.0 |
| 8 | 0.483 | 96.6% | 15.0 | 16.0 |
| 9 | 0.462 | 92.4% | 25.0 | 22.4 |
| 10 | 0.415 | 83.0% | 5.6 | 6.4 |
| | | MEANS: | 12.18 | 12.09 |

The mean retention of dust for both experiments is 90.48% and the mean allergen concentrations in retained dust are virtually identical to that of the original dust sample. It will be noted that even at the lower percentage retentions, the allergen concentration remains the same.

EXAMPLE 10

Data on serial collection of samples from the same area

An area of 18 inches by 12 inches was marked out with masking tape on a Living room carpet in a house. This area was serially sampled with consecutive devices, in the normal vacuum cleaning manner, for the times stated. The recovered dust samples were each weighed and the allergen content measured with the U.C.D. modified assay.

TABLE 9

Data on dust recovered in serial samples from the same carpet area in two houses

| Sample | Time | House Weight (g) | µg/g | Total allergen (µg) |
|---|---|---|---|---|
| 1 | 15 sec. | 0.414 | 4.8 | 1.99 |
| 2 | 15 sec. | 0.311 | 8.0 | 2.49 |
| 3 | 15 sec. | 0.297 | 9.6 | 2.85 |
| 4 | 15 sec. | 0.229 | 9.2 | 2.11 |
| | total for 1st min. | 1.257 | 7.9 | 9.44 |
| 5 | 30 sec. | 0.592 | 4.8 | 2.84 |
| 6 | 30 sec. | 0.271 | 7.2 | 1.95 |
| | total for 2nd min. | 0.863 | 6.0 | 4.79 |
| 7 | 1 min. | 0.321 | 4.8 | 1.54 |
| 8 | 1 min. | 0.192 | 6.8 | 1.31 |
| 9 | 1 min. | 0.216 | 6.8 | 1.47 |
| 10 | 1 min. | 0.199 | 6.4 | 1.27 |
| 11 | 1 min. | 0.132 | 6.4 | 0.84 |
| 12 | 2 min. | 0.265 | 6.8 | 0.9/min. |

The above data shows that it is extremely difficult to remove all dust and allergen from carpets, even over extensive multiple sampling episodes. The concentration of allergen recovered from each sample is virtually identical during each of the same sampling periods over the experimental time of 9 minutes, using the device according to the invention. However, the total allergen recovered per minute falls by 50% from the first to the second minute and by ten-fold over the 9 minute sampling period. Therefore, the device is remarkably efficient at showing the concentration of antigen (i.e. µg/g dust). However, it clearly demonstrates the ability of the device according to the invention to measure the true level of allergen present in a given area. This is the first reported demonstration of this effect and was only made possible by the device according to the invention.

EXAMPLE 11

Data showing the large variation in amounts of allergen present in different areas of the same room, using both bags and devices according to the invention Weights of dust samples collected in bags in Example 12 were compared with those collected from the same areas using devices according to the invention immediately thereafter. The Coefficient of Variation (CV) in weights of dust shown in column 2 in Table 10 (bags) and the sum of weights collected in each of the four devices used per one square metre area in Table 11 (devices), were calculated. The CV for bags was 87% and for devices it was 43%. None of the devices was filled to capacity. Since it has been demonstrated herein that the devices according to the invention reliably retain more than 90% of all dust collected and since none of the devices was filled to capacity, it follows that the high CV values obtained for both bags and devices are due to real variations in the dust (and allergen) levels detected in different areas. The very high CV obtained in the case of bags is evidence of the unreliability of bags for collecting samples compared with the devices according to the invention. This Example also demonstrates the need for multi-site sampling.

EXAMPLE 12

Comparison of levels of allergen collected by bags and devices according to the invention expressed as concentration (µg/g dust) or per unit area (µg/m$^2$)

A typical living room was divided up into 13×1 square metre areas marked out with masking tape. Each area was individually vacuum cleaned in a standard manner by passing the cleaner head up and down the area twice over for a total period of two minutes per square metre using individual standard vacuum cleaner paper bags to collect the sample in each area. Immediately afterwards each square meter was further divided by four into a total of 52 one-quarter square meter and each of these was sampled for 30 seconds with the device according to the invention: All samples were weighed. All samples from bags were processed and tested by the standard (sieving) method. The device samples were tested in the U.C.D. modified assay, as described in Example 2. Allergen levels were expressed as concentration (µg/g dust) and as amount per unit area (µg/m$^2$) and R values calculated. The results are shown in Tables 10 and 11.

TABLE 10

| | Bags | | |
|---|---|---|---|
| Area No. | Weight dust (g) | Der pI µg/g dust | µg/m$^2$ |
| 1 | 1.071 | 8.8 | 9.41 |
| 2 | 1.98 | 12.0 | 23.76 |
| 3 | 0.273 | 11.6 | 3.13 |
| 4 | 1.034 | 12.0 | 12.40 |
| 5 | 0.890 | 13.2 | 11.74 |
| 6 | 0.700 | 11.6 | 8.12 |
| 7 | 3.630 | 10.0 | 36.30 |
| 8 | 0.070 | 1.6 | 0.112 |
| 9 | 0.849 | 10.8 | 9.169 |
| 10 | 1.644 | 16.6 | 27.619 |
| 11 | 0.101 | 9.6 | 0.969 |
| 12 | 0.210 | 12.8 | 2.680 |
| 13 | 1.22 | 10.0 | 12.20 |

The Correlation Coefficient, R, between results expressed as µg/g and µg/m$^2$=0.45; p=0.158, not significant (i.e. no correlation).

TABLE 11

| | Device | | | |
|---|---|---|---|---|
| Area No. Bag | Area No. Device | Weight dust (g) | Der pI µg/dust | Der pI µa/m$^2$ |
| 13 | 1 | 1.383 | 6.4 | 8.857 |
| | 2 | 1.836 | 1.6 | 1.650 |
| | 3 | 0.786 | 10.4 | 8.170 |
| | 4 | 0.486 | 6.4 | 3.110 |
| 1 | 5 | 0.333 | 4.8 | 1.59 |
| | 6 | 0.620 | 12.0 | 7.44 |
| | 7 | 0.576 | 10.4 | 5.99 |
| | 8 | 0.536 | 7.6 | 4.07 |
| 2 | 9 | 0.546 | 9.6 | 5.24 |
| | 10 | 0.496 | 8.8 | 4.36 |
| | 11 | 0.787 | 12.4 | 9.75 |
| | 12 | 0.553 | 5.2 | 2.87 |
| 3 | 13 | 1.176 | 8.0 | 9.408 |
| | 14 | 0.742 | 9.2 | 6.820 |
| | 15 | 0.623 | 16.8 | 10.460 |
| | 16 | 0.424 | 13.2 | 5.590 |
| 4 | 17 | 0.690 | 10.8 | 7.452 |

TABLE 11-continued

| | | Device | | |
|---|---|---|---|---|
| Area No. Bag | Area No. Device | Weight dust (g) | Der pI µg/dust | Der pI µa/m² |
| | 18 | 1.096 | 6.3 | 7.014 |
| | 19 | 0.402 | 7.6 | 3.055 |
| | 20 | 0.593 | 12.0 | 7.116 |
| 5 | 21 | 0.571 | 7.6 | 3.883 |
| | 22 | 0.333 | 9.2 | 3.062 |
| | 23 | 0.576 | 8.8 | 5.068 |
| | 24 | 0.346 | 10.4 | 3.598 |
| 8 | 25 | 0.846 | 4.8 | 4.06 |
| | 26 | 1.034 | 8.0 | 8.27 |
| | 27 | 0.945 | 4.0 | 3.78 |
| | 28 | 0.686 | 3.2 | 2.195 |
| 7 | 29 | 1.149 | 1.6 | 1.818 |
| | 30 | 1.157 | 3.6 | 4.14 |
| | 31 | 1.256 | 4.0 | 5.024 |
| | 32 | 0.706 | 1.6 | 1.120 |
| 6 | 33 | 0.474 | 1.6 | 1.576 |
| | 34 | 0.196 | 3.2 | 0.705 |
| | 35 | 0.340 | 3.6 | 3.536 |
| | 36 | 0.202 | 10.4 | 1.449 |
| 11 | 37 | 0.555 | 15.2 | 8.436 |
| | 38 | 0.207 | 3.2 | 0.662 |
| | 39 | 0.262 | 5.2 | 1.362 |
| | 40 | 0.241 | 1.6 | 0.385 |
| 12 | 41 | 0.383 | 1.6 | 0.612 |
| | 42 | 0.575 | 6.4 | 3.296 |
| | 43 | 0.379 | 9.6 | 2.676 |
| | 44 | 0.474 | 2.0 | 0.948 |
| 10 | 45 | 0.588 | 8.8 | 5.174 |
| | 46 | 0.603 | 7.6 | 4.582 |
| | 47 | 0.666 | 10.4 | 6.926 |
| | 48 | 0.226 | 2.4 | 5.42 |
| 9 | 49 | 0.055 | 1.6 | 0.088 |
| | 50 | 0.576 | 4.0 | 2.064 |
| | 51 | 0.206 | 1.6 | 0.329 |
| | 52 | 0.203 | 4.0 | 0.812 |

The Correlation Coefficient, R, between results expressed as µg/g and µg/m²=0.745 p=<0.0001, very significant (i.e. correlation very good). The R values clearly demonstrate that the devices according to the invention show a very significant correlation (p=<0.0001) between allergen levels expressed as µg/g or as µg/m², which is the expected result. However, the bags show no significant correlation (p=0.158) between the two methods of expressing allergen levels. We believe that this is due to the poor collection efficiencies of the paper bags (as delineated) giving a large standard deviation in sample weights collected.

EXAMPLE 13

Comparison of bags and devices according to the invention used for collecting samples from two square meter areas in nine rooms from eight difference houses Two square meter areas approximately in the middle of each room were divided into four half square meter areas. Samples were taken for two diagonally opposite half-square meters each for two separate bags and the remaining two diagonally opposite areas using two separate devices according to the invention. The dust samples were weighed as before and sieved in the case of bags (as per standard method) and tested for allergen levels as before. Allergen levels were expressed as both µg/g and µg/m² and R values calculated.

The results are shown in Table 12.

TABLE 12

Comparison of bags and devices from sampling in nine rooms from eight houses

| | BAGS | | | DEVICES | | |
|---|---|---|---|---|---|---|
| House ID. | µg/g | | µg/m² | µg/g | | µg/m² |
| E | 52.0 | B1 | 35.36 | 10.0 | D1 | 1.03 |
| | 40.0 | B2 | 5.6 | 14.0 | D2 | 0.7 |
| P | 9.6 | B1 | 23.71 | 6.4 | D1 | 13.09 |
| | 6.0 | B2 | 20.76 | 4.8 | D2 | 8.35 |
| F | 8.8 | B1 | 15.84 | 6.4 | D1 | 19.23 |
| | 3.6 | B2 | 5.18 | 2.4 | D2 | 8.044 |
| A | 12.4 | B1 | 0.862 | 40.0 | D1 | 12.04 |
| | 24.0 | B2 | 3.36 | 40.0 | D2 | 11.2 |
| B(i) | 0.8 | B1 | 0.12 | 2.8 | D1 | 0.38 |
| | 0.8 | B2 | 0.056 | 10.0 | D2 | 4.920 |
| B(ii) | 3.2 | B1 | 4.35 | 7.2 | D1 | 0.652 |
| | 5.2 | B2 | 7.33 | 0.8 | D2 | 4.92 |
| B(iii) | 50.0 | B1 | 25.05 | 20.0 | D1 | 7.62 |
| | 11.2 | B2 | 4.36 | 50.0 | D2 | 20.25 |
| H1 | 12.4 | B1 | 17.09 | 14.4 | D1 | 12.97 |
| | 30.0 | B2 | 11.64 | 20.8 | D2 | 23.62 |
| H2 | 80.0 | B1 | 2.4 | 38.0 | D1 | 21.92 |
| | 80.0 | B2 | 29.6 | 43.0 | D2 | 28.8 |
| R value = | 0.420 | | | 0.627 | | |
| p = | 0.082 | | | 0.0053 | | |
| Significance: | Some | | | Very | | |

This data again shows that the device according to the invention give the expected results that allergen expressed as µg/g dust correlates with allergen expressed as µg/m²; however, the bags give only a poor correlation in this experiment.

Taking the results of Examples 10, 11, 12 and 13, together they provide overwhelming evidence that bags are unreliable for collecting dust samples and that the device according to the invention is much more reliable, and is capable of measuring true levels of allergen in a given area. Additionally, the device according to the invention has the many advantages and conveniences outlined below.

The utility and advantages of the antigen collection apparatus according to the invention relative to conventional apparatus will be apparent from Examples 9–13.

The poor collection quality of paper vacuum cleaner bags relative to collection apparatus according to the invention will be clearly apparent from Examples 11–13.

Experiments carried out in connection with the present invention as described in the Examples have demonstrated that dust-sampling using vacuum cleaner bags is subject to serious errors, especially when applied to small areas. The problems can be summarized as follows:

a) Small amounts of dust and allergen are difficult to recover from paper bags, because the particles become partially embedded in the paper.

b) Dust and fluff residues lodged in the flexible plastics fibbings and the metal and plastics components of vacuum cleaner hoses and may easily become dislodged, thus contaminating subsequent dust-samples.

c) There are very large variations in dust and allergen levels in adjacent small areas (for example, ¼ square metre or ½ square metre areas) of rooms. The devices according to the invention have demonstrated for the first time the existence of such statistically valid variations.

d) Concentrations of allergens tend to be at a maximum in frequently used areas of rooms, such as in the centre, in front of regularly used chairs and beside beds. Furthermore, it is these areas where dust and allergen are more likely to be disturbed and become inhaled.

e) It is demonstrated herein that the total dust and allergen collection efficiency of the collection device according to the invention exceeds a mean of 92.5% (i.e. a Coefficient of Variation of <7.5%); therefore the large variations in dust collected in small adjacent areas are not due to device collection variation or losses.

f) In the case of the collection device according to the invention it has been demonstrated that the Correlation Coefficient equals 0.745 (p=0.0001, highly significant) when one compares the concentration of allergen in dust (µg/g) with the mount of allergen present per unit area (during a fixed sampling time). However if the standard paper bag method is used for comparing the two units of measurement, the r value is only 0.45 (p=0.158, not significant).

Therefore it can be concluded from experiments described in the Examples that in order to accurately measure the potential for allergen exposure (which is clearly the parameter that matters most to the patient) in a room, one should:

1) Sample at more than one site in a room;

2) Sample in places most likely to contain significant allergen levels; and

Express one's result as total allergen per unit area for example, µg/m$^2$, the total amount of other material being less relevant.

It will be appreciated that the sample collection device according to the invention is far more effective and accurate than the sampling devices used up to now, and has the following advantages:

a) It is small, convenient and not easily damaged.

b) It is easy and clean to handle, minimising direct contact by the householder with the sample material or dust, which can be unpleasant at best, and dangerous in an allergic person at worst.

c) There is minimal chance of cross-contamination of samples by material previously lodged in vacuum cleaner components since the device can normally be positioned upstream of the hose.

d) With small samples, more than 90% of the sample is reliably and reproducibly recoverable in the collection device, which is not the case with vacuum cleaner bags.

e) The user does not have to dismantle the vacuum cleaner or remove or change bags or go to the expense of using a new bag, in order to carry out an allergen test.

f) The device is quick and simple to use.

g) The sample collected by the device does not need to be processed, sieved or handled in any way prior to the test, so the device becomes part of the testing process.

h) The device may be coated directly with assay reagents, such as antibody, thus, eliminating one or more steps in the assay.

i) The device makes it possible (for the first time) to accurately measure the total allergen content in a given area independently of the amount of dust present.

We claim:

1. Apparatus for collection of antigen dispersed in a motile fluid in an environment, comprising:

(i) a device having an inlet for said motile fluid and means for connection to an air suction means of a vacuum cleaner, said inlet and said connection means being disposed relative to one another to define a fluid path therebetween;

(ii) means for collecting and retaining the antigen when said antigen comes into contact therewith, by virtue of the fluid carrying the antigen impinging on or passing therethrough;

(iii) said collecting and retaining means being received by or integral with, said device such that it is disposed in said fluid path; and (iv) an antigen binding surface with immobilized antibodies specific for said antigen, integral with or forming part of said collecting and retaining means for bringing said antigen into contact with said antibodies for confirming the presence of or quantifying said antigen.

2. Apparatus according to claim 3, wherein the coated surface is a solid phase for an immunoassay.

3. Apparatus according to claim 1, wherein the antigen binding surface is a fluid porous surface.

4. Apparatus according to claim 3, wherein the fluid porous surface is accommodated in said device and wherein said device further comprises a tube for insertion intermediate said air suction means and a sweeping attachment.

5. Apparatus according to claim 3, wherein the fluid porous surface is composed of a porous plastic material.

6. Apparatus according to claim 3, wherein the fluid porous surface is composed of porous, sintered styrene.

7. Apparatus according to claim 3, wherein the fluid porous surface is composed of a porous, protein-binding plastic material.

8. Apparatus according to claim 3, wherein the fluid porous surface is composed of an element having a shape corresponding substantially to the shape of said device.

9. Apparatus according to claim 8, wherein the fluid porous surface comprises a nylon gauze.

10. Apparatus according to claim 8, which includes a filter for collecting a major proportion of any dust present in a fluid stream passing therethrough or impinging thereon.

11. Apparatus according to claim 3, wherein the porous material has pores having an average diameter in the range 5–300 µm.

12. Apparatus according to claim 1, wherein the antibody is bound to the surface by means of particles coated with said antibody.

13. Apparatus according to claim 1, wherein the device includes a fluid porous disc for entrapment of debris in said fluid path upstream of said collecting and retaining means.

14. Apparatus according to claim 1, wherein the antigen binding surface is removable.

15. Apparatus according to claim 1, wherein the environment is the household environment.

16. Apparatus according to claim 1, wherein the antigen is a micro-orgasm or fungus.

17. Apparatus according to claim 1 wherein the antigen is an allergen.

18. Apparatus according to claim 17, wherein said allergen is selected from the group consisting of cat-dander allergen, dog-dander allergen, an insect allergen, pollen and fungal spores.

19. Apparatus according to claim 18, wherein said insect allergen is dust-mite allergen.

20. A kit comprising a container containing apparatus for collection of antigen dispersed in a motile fluid in a given environment, comprising:

(i) a device having an inlet and means for connection to an air suction means of a vacuum cleaner, said inlet and said connection means being relative to one another to define a fluid path therebetween;

(ii) means for collecting and retaining the antigen when said antigen comes into contact therewith, by virtue of the fluid carrying the antigen impinging on or passing therethrough;

(iii) said collecting and retaining means being received by or integral with said device such that it is disposed in said fluid path; and (iv) an antigen binding surface with immobilized antibodies specific for said antigen, integral with or forming pan of said collecting and retaining means, for bringing said antigen into contact with said antibodies for confirming the presence of or quantifying said antigen.

21. A kit according to claim 20, wherein the antigen is dust-mite allergen.

22. A kit according to claim 21, which includes a bottle containing an extraction medium which comprises a buffer containing a dust-mite allergen extracting amount of chitinase.

23. A method for collection and detection of antigen dispersed in a motile fluid in a given environment, which comprises the steps of:

(i) providing the apparatus of claim 1;

(ii) drawing a fluid containing or suspected of containing the antigen through the inlet of said device;

(iii) collecting an antigen by retaining the antigen on said antigen binding surface of the device when the antigen comes into contact therewith, by virtue of the fluid carrying the antigen impinging on or passing through the surface; and (iv) detecting said antigen with the antigen binding surface in situ following detachment of the device from said device.

24. A method according to claim 23, wherein the antigen is detected by enzyme immunoassay.

25. A method according to claim 24, wherein the assay used is a sandwich assay.

26. A method according to claim 23, wherein the detection of antigen is semi-quantitative.

* * * * *

UNITED STATES PATENT AND TRADEMARK OFFICE
CERTIFICATE OF CORRECTION

PATENT NO. : 5,679,535

DATED : October 21, 1997

INVENTOR(S) : Joyce et al.

It is certified that error appears in the above-indentified patent and that said Letters Patent is hereby corrected as shown below:

On the cover, in the section titled References Cited, U.S. Patent Documents, line 3, change "Valkins" to -- Valkirs --.

In column 5, line 22, change "bny" to -- by --.

In column 5, lines 22-23, change "immunoasay" to -- immunoassay --.

In column 5, line 54, change "arid" to -- and --.

In column 7, line 65, change "faecal" to -- fecal --.

In column 11, line 13, change "alter" to -- after --.

In column 15, line 65, change "plastics" to -- plastic --.

In column 16, line 9, change "degree" to -- about --.

UNITED STATES PATENT AND TRADEMARK OFFICE
CERTIFICATE OF CORRECTION

PATENT NO. : 5,679,535
DATED : October 21, 1997
INVENTOR(S) : Joyce et al.

It is certified that error appears in the above-indentified patent and that said Letters Patent is hereby corrected as shown below:

In column 16, line 17, change "robe" to -- tube --.

In column 17, line 42, after "500" change "l" to -- $\mu$l --.

In column 18, line 63, change "Living" to -- living --.

In column 20, line 15, change "metres" to --meter--.

In column 20, line 16, change ":" to -- . --.

In column 20, line 52, in the caption to the last column of Table 11, change "$\mu$a/m$^2$" to -- $\mu$g/m$^2$ --.

In column 21, in the 12th line of the last column of Table 11, change "1.818" to -- 1.838 --.

UNITED STATES PATENT AND TRADEMARK OFFICE
CERTIFICATE OF CORRECTION

PATENT NO. : 5,679,535
DATED : October 21, 1997
INVENTOR(S) : Joyce et al.

It is certified that error appears in the above-indentified patent and that said Letters Patent is hereby corrected as shown below:

In column 22, in the 1st line of the heading of Table 12, after "devices" change "from" to -- for --.

In column 22, line 58, change "fibbings" to -- ribbings --.

In column 23, line 16, change "mount" to -- amount --.

In column 23, line 29, before "Express" insert -- 3) --.

In Claim 20, column 25, line 12, change "pan" to -- part --.

Signed and Sealed this

Second Day of November, 1999

Q. TODD DICKINSON

Attest:

Attesting Officer

Acting Commissioner of Patents and Trademarks